US010222350B2

(12) United States Patent
Gunawan

(10) Patent No.: US 10,222,350 B2
(45) Date of Patent: Mar. 5, 2019

(54) HIGH SENSITIVITY FORCE GAUGE WITH PARALLEL DIPOLE LINE TRAP SYSTEM

(71) Applicant: International Business Machines Corporation, Armonk, NY (US)

(72) Inventor: Oki Gunawan, Westwood, NJ (US)

(73) Assignee: International Business Machines Corporation, Armonk, NY (US)

(*) Notice: Subject to any disclaimer, the term of this patent is extended or adjusted under 35 U.S.C. 154(b) by 36 days.

(21) Appl. No.: 15/647,923

(22) Filed: Jul. 12, 2017

(65) Prior Publication Data

US 2019/0017965 A1   Jan. 17, 2019

(51) Int. Cl.
*G01L 5/00* (2006.01)
*G01N 27/72* (2006.01)

(52) U.S. Cl.
CPC ............. *G01N 27/72* (2013.01); *G01L 5/00* (2013.01)

(58) Field of Classification Search
CPC ...................................................... G01L 5/00
See application file for complete search history.

(56) References Cited

U.S. PATENT DOCUMENTS

| 3,492,738 | A | 2/1970 | Simon |
| 5,396,136 | A | 3/1995 | Pelrine |
| 7,252,001 | B2 | 8/2007 | Boletis et al. |
| 7,597,002 | B2 | 10/2009 | Moser et al. |
| 8,895,355 | B2 | 11/2014 | Cao et al. |
| 9,041,389 | B2 | 5/2015 | Gokmen et al. |
| 9,093,377 | B2 | 7/2015 | Cao et al. |
| 9,236,293 | B2 | 1/2016 | Cao et al. |
| 2014/0253114 | A1 | 9/2014 | Khamesee et al. |
| 2015/0064806 | A1* | 3/2015 | Cao ........................ H01L 21/283 438/3 |
| 2016/0005646 | A1* | 1/2016 | Cao ........................ H01L 21/283 438/3 |
| 2017/0045433 | A1 | 2/2017 | Gunawan et al. |

OTHER PUBLICATIONS

Leckband et al., "Forces controlling protein interactions: theory and experiment," Colloids and Surfaces B: Biointerfaces 14 (Aug. 1999) pp. 83-97.
Gunawan et al., "A parallel dipole line system," Applied Physics Letters 106, pp. 062407-1-5 (Feb. 2015) (5 pages).
Gunawan et al., "A Diamagnetic Trap with 1D Camelback Potential," arXiv preprint, arXiv:1405.5220, May 2014, (5 pages).
M. Boukallel et al., "Levitated micro-nano force sensor using diamagnetic materials," International Conference on Robotics and Automation, Sep. 2003, vol. 3, pp. 3219-3224.

* cited by examiner

*Primary Examiner* — Clayton E Laballe
*Assistant Examiner* — Jas Sanghera
(74) *Attorney, Agent, or Firm* — Vazken Alexanian; Michael J. Chang, LLC

(57) ABSTRACT

A high sensitivity force gauge using a magnetic PDL trap system is provided. In one aspect, a force gauge includes: a PDL trap having a pair of dipole line magnets and a diamagnetic rod levitating above the dipole line magnets; an actuator with an extension bar adjacent to the PDL trap; a first object of interest attached to the diamagnetic rod; and a second object of interest attached to the extension bar, wherein the actuator is configured to move the second object of interest toward or away from the PDL trap via the extension bar. A method for force measurement using the present force gauge is also provided.

20 Claims, 7 Drawing Sheets

TOP VIEW

HIGH SENSITIVITY FORCE GAUGE WITH PARALLEL DIPOLE LINE TRAP SYSTEM

FIELD OF THE INVENTION

The present invention relates to magnetic parallel dipole line (PDL) trap systems, and more particularly, to a high sensitivity force gauge using a PDL trap system.

BACKGROUND OF THE INVENTION

There is often a need to perform very small force measurements involving various objects with weak interactions, such as Van der Walls forces, chemical bonding forces and Casimir forces. See, for example, Leckband et al., "Forces controlling protein interactions: theory and experiment," Colloids and Surfaces B: Biointerfaces 14 (August 1999) pgs. 83-97. Conventional measurement techniques in this system are, however, complex and costly.

Therefore, an improved high-sensitivity force gauge would be desirable.

SUMMARY OF THE INVENTION

The present invention provides a high sensitivity force gauge using a magnetic parallel dipole line (PDL) trap system. In one aspect of the invention, a force gauge is provided. The force gauge includes: a PDL trap having a pair of dipole line magnets and a diamagnetic rod levitating above the dipole line magnets; an actuator with an extension bar adjacent to the PDL trap; a first object of interest attached to the diamagnetic rod; and a second object of interest attached to the extension bar, wherein the actuator is configured to move the second object of interest toward or away from the PDL trap via the extension bar.

In another aspect of the invention, a method for force measurement is provided. The method includes: providing a force gauge comprising a PDL trap having a pair of dipole line magnets, a diamagnetic rod levitating above the dipole line magnets, and an actuator with an extension bar adjacent to the PDL trap; attaching a first object of interest to the diamagnetic rod; attaching a second object of interest to the extension bar; moving the second object of interest toward or away from the PDL trap via the extension bar; and measuring a displacement of the diamagnetic rod in the PDL trap as a function of a position of the second object of interest.

A more complete understanding of the present invention, as well as further features and advantages of the present invention, will be obtained by reference to the following detailed description and drawings.

DETAILED DESCRIPTION OF PREFERRED EMBODIMENTS

Figure 1:
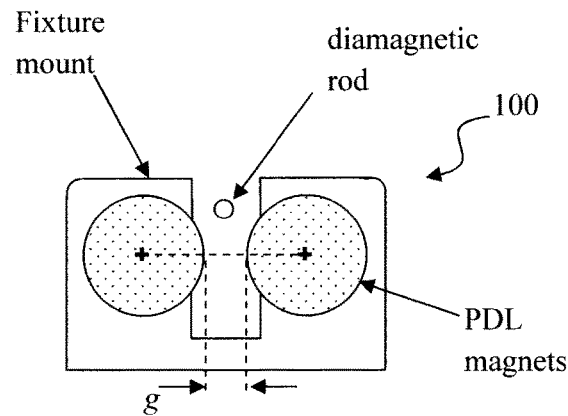
FIG. 1 is a front view diagram illustrating an exemplary parallel dipole line (PDL) trap-based force gauge according to an embodiment of the present invention.

Provided herein is a high-sensitivity force gauge utilizing a parallel dipole line (PDL) trap system consisting of a pair of transverse cylindrical magnets (TCMs). A diamagnetic cylindrical rod such as a diamagnetic (e.g., graphite) rod is trapped at the center of the trap. The diamagnetic cylindrical rod is confined in a weak one-dimensional camelback magnetic potential along the longitudinal axis of the trap that provides stable trapping. See, for example, Gunawan et al., "A parallel dipole line system," Applied Physics Letters 106, pp. 062407-1-5 (February 2015) (hereinafter "Gunawan"); and U.S. Pat. No. 8,895,355, U.S. Pat. No. 9,093,377, and U.S. Pat. No. 9,236,293 all issued to Cao et al., entitled "Magnetic Trap for Cylindrical Diamagnetic Materials," the contents of all of which are incorporated by reference as if fully set forth herein.

The diamagnetic rod is attached to a first object of interest (an object for which an interacting force is to be measured). A second object of interest is attached to an actuator mechanism that enables the position of the second object to be adjusted (relative to the first object). According to an exemplary embodiment described in detail below, the actuator mechanism includes an extension bar driven by a piezo ceramic actuator (which generates linear motion of the extension bar based on an applied voltage).

The actuator mechanism moves the second object on the extension bar toward or away from the first object attached to the diamagnetic rod. As the second object on the extension bar is brought closer to the first object, an interacting force between the objects will cause the first object (and the diamagnetic rod to which it is attached) to be pulled toward or repelled away from the second object. By analyzing this displacement versus the position of the (second) object, the interacting force between the objects can be determined as a function of distance.

The details of a PDL trap system as they pertain to the present techniques will become apparent from the description provided below. In general however, a PDL trap consists of a magnetic parallel dipole line system made of a pair of transversely magnetized (also called diametric) cylindrical magnet that naturally join together. The magnets have an elongated shape such as a cylinder, bar, or stripe, whose magnetization is in the transverse direction (perpendicular to the long axis). These magnets will be referred to herein as "dipole line" or "diametric" magnets. A diamagnetic cylindrical object such as a graphite rod can be trapped at the center and will levitate above the pair of diametric magnets. The key discovery and the central feature of the PDL trap is the existence of a "camelback magnetic potential" along the longitudinal (z-axis), i.e., magnetic field enhancement near the edge of the dipole line which occurs for diametric magnet with length exceeding the critical length $L_C$ where $L_C \sim 2.5a$ for a pair of cylindrical diametric magnet system, wherein a is the radius of the magnet.

The cylindrical magnets in a PDL trap do not, however, have to be in contact with one another. For instance, a gap g can be opened between the magnets and the field distribution will be identical except scaled down by a constant. See, for example, U.S. patent application Ser. No. 15/131, 566 by Gunawan, entitled "Parallel Dipole Line Trap with Variable Gap and Tunable Trap Potential" (hereinafter "U.S. patent application Ser. No. 15/131,566"), the contents of which are incorporated by reference as if fully set forth herein. As long as the gap is kept less than a critical gap $g_C$ (i.e., where the rod falls through the trap), the diamagnetic rod will remain levitating above the magnets. See, e.g., Equation 5 of U.S. patent application Ser. No. 15/131,566. One notable advantage to opening a gap between the magnets is that it opens up space between the magnets to fit in various apparatus or experiments, e.g., allowing an optical beam to pass vertically (between the magnets) for object detection. Another notable advantage is that a gap permits the objects of interest to fit in the space between the magnets and move freely back and forth during operation.

A number of different techniques can be employed to open up a gap between the magnets in a PDL trap. For instance, a fixed size spacer can be placed between the magnets, wherein the size of the spacer equates to the size of the gap. While spacers of varying sizes can be swapped to change the size of the gap, each spacer is of a fixed dimension. For a more tunable system, a variable gap fixture can be employed in which the magnets are each attached to separate mounts, and the mounts can be moved closer or farther apart from one another (e.g., using an adjustable screw mechanism). Detailed descriptions/depictions of both fixed spacer and variable gap fixtures for creating a gap between the magnets are provided in U.S. patent application Ser. No. 15/131,566. While a variable gap fixture is used in the following description, this is merely an example, and a fixed spacer could be implemented in the same manner described.

An exemplary force gauge 100 in accordance with the present techniques is now described in detail by way of reference to FIGS. 1 (front view) and 2 (top-down view). As shown in FIG. 1, force gauge 100 includes a PDL trap having a pair of cylindrical magnets (labeled "PDL magnets") mounted to a fixture (labeled "fixture mount"), and a diamagnetic rod (e.g., a graphite rod) levitating above the magnets. As shown in FIG. 1, the fixture introduces a gap g between the magnets. As described above, having a gap between the magnets enables optical sensors to be used to register a position of the diamagnetic rod in the PDL trap (e.g., where a light source and light sensors are located at a top/bottom of the PDL trap such that the diamagnetic rod can pass therebetween—see below).

The fixture mount can introduce a 'fixed' gap g between the magnets (as shown in FIG. 1) or, as described above, can include a screw mechanism that moves the mounts (separately attached to the magnets) closer or farther apart to vary the gap. Also, as described above, a fixed spacer can instead be employed between the magnets to open up the gap.

Figure 2:
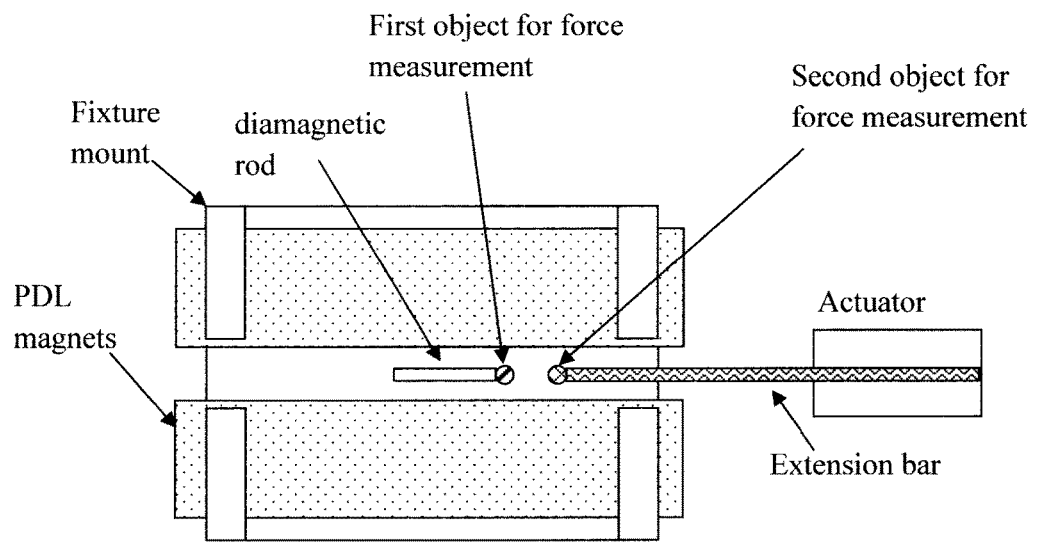
FIG. 2 is a top-down diagram illustrating the PDL trap-based force gauge according to an embodiment of the present invention.

The actuator mechanism can be seen when force gauge 100 is viewed from the top. See FIG. 2. As shown in FIG. 2, the actuator mechanism is located to one side of the PDL trap, and includes an actuator which controls movement of an extension bar (towards or away from) the PDL trap—see below).

According to an exemplary embodiment, the actuator is a piezo ceramic actuator that generates linear motion of the extension bar based on an applied voltage. Piezo ceramic actuators are commercially available, for example, from PI (Physik Intrumente) LP, Auburn, Mass. The extension bar preferably is formed of a non-ferromagnetic material such as plastic, acrylic, or non-magnetic metal such as copper and/or brass.

As shown in FIG. 2, a first object of interest is attached to the diamagnetic rod, and a second object of interest is attached to the extension bar. Notably, the first object is attached to an end of the diamagnetic rod proximate/facing the extension bar, and the second object is attached to an end of the extension bar proximate/facing the diamagnetic rod. In general, any two objects can be implemented between which an interacting force is desired to be measured using force gauge 100. By way of example only, object 1 and object 2 can be any test material such as metals or synthetic materials, and/or biomaterials such as proteins, genetic materials (such as deoxyribonucleic acid (DNA) or ribonucleic acid (RNA)) or inorganic materials such as molecules and/or compounds, metals, etc. The objects under test can be attached at the tip of the graphite rod and the end of the extension bar (see, e.g., FIG. 2) using, for example, an adhesive like an epoxy glue. By way of example only, the interactions between the objects that are measured can be electrostatic forces, Van der Walls or Cashimir forces. The size of the objects being tested is limited by the condition that the supporting diamagnetic rod must still be levitating. Specifically, if the object attached to the rod is too large then the rod will no longer be levitating.

Figure 3:
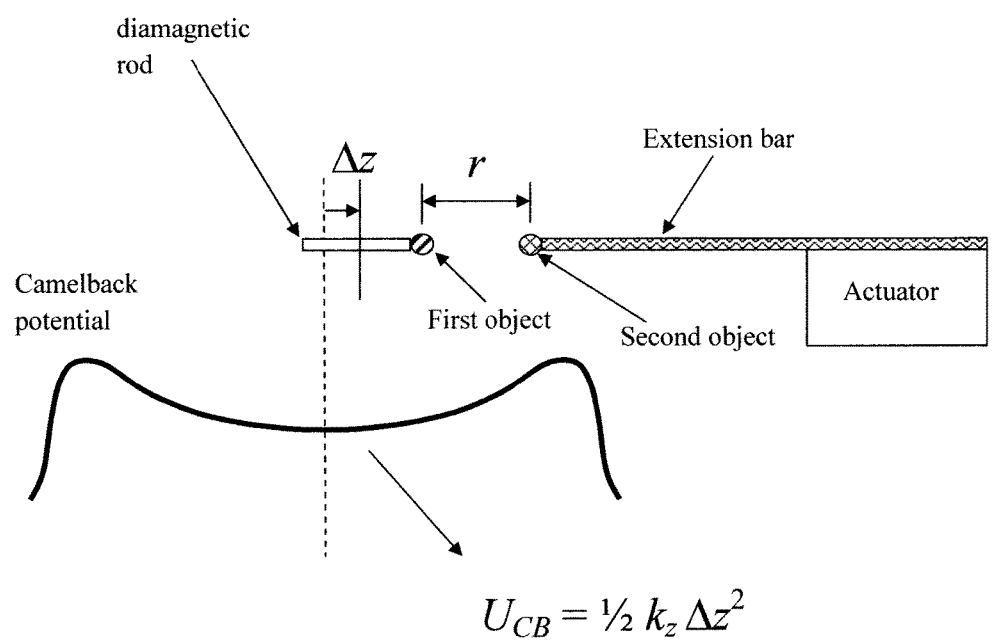
FIG. 3 is a diagram illustrating the principles of operation of the present force gauge according to an embodiment of the present invention.

The principles of operation of the present force gauge are now described in further detail by way of reference to FIG. 3. As described above, the first object of interest is attached to the diamagnetic rod (levitating above the PDL trap) and the second object of interest is attached to the extension bar controlled by the actuator. When the second object on the extension bar is brought closer to the first object, an interacting force between the objects will cause the first object (and the diamagnetic rod to which it is attached) to be pulled toward the second object (or repelled away from—depending on the force). By analyzing this displacement versus the position of the (second) object, the interacting force between the objects can be determined as a function of distance. See FIG. 3.

Specifically, the diamagnetic rod sits on the PDL camelback magnetic potential $U_{CB}$ with spring constant $k_z$. This spring constant can be determined from the resonant frequency of the trap given as: $k_z = \omega^2$ m, where $\omega = 2\pi f$ and f is the angular frequency of the trap. As provided above, the camelback magnetic potential exists along the longitudinal axis (z-axis) of the PDL trap. When the extension bar is actuated (via the actuator) bringing the second object closer to the first object, the first object/diamagnetic rod will move within the trap by $\Delta z$, due to the interacting force between the objects. For instance, when there is an attracting force between the first and second objects, bringing the second object towards the first object will move the first object/ diamagnetic rod toward the second object (in this case to the right side of the PDL trap). However, when there is a repulsion force between the first and second objects, bringing the second object towards the first object will move the first object/diamagnetic rod away from the second object (in this case to the left side of the PDL trap). The former case (attractive force) is shown illustrated in FIG. 3, however the same principles apply in either case. The displacement of the diamagnetic rod $\Delta z$ is measured as a function of the separation of the first and second objects (r). Thus we can obtain the force F as a function of distance r, i.e., F(r), between the first object and the second object:

$$F(r)=k_z\Delta z.$$

Preferably, the extension bar is moved to obtain another value of r, and the measurement based on the change in displacement of the rod $\Delta z$ is repeated one or more additional times. This will help establish the distance dependence laws for the objects (i.e., how the force scales with the distance between the objects).

Figure 4:
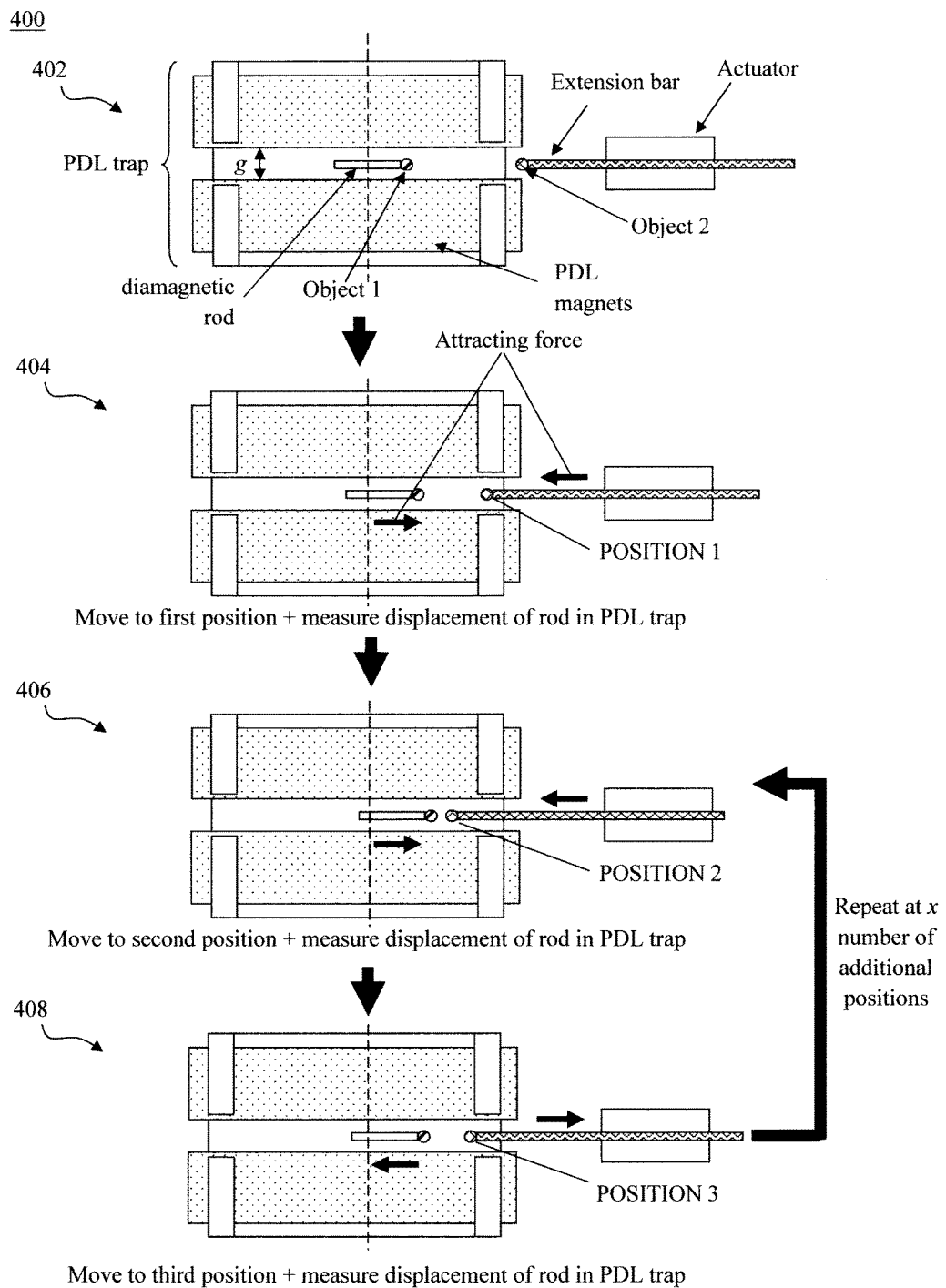
FIG. 4 is a top-down diagram illustrating an exemplary methodology for operating the present force gauge in the case where attracting forces between objects are present according to an embodiment of the present invention.

An exemplary method for operating the present force gauge is now described by way of reference to methodology 400 of FIG. 4, shown as top-view depictions of the force gauge. As shown in step 402, the above-described PDL force gauge is provided having a pair of cylindrical magnets mounted to a fixture (introducing a gap g between the magnets), a diamagnetic rod (e.g., a graphite rod) levitating above the magnets, and an actuator (e.g., a piezo ceramic actuator) with extension bar off to one side of the PDL trap. A first object of interest is attached to the diamagnetic rod, and a second object of interest is attached to the extension bar. See step 402 in FIG. 4. The PDL force gauge will be used to measure the (attracting or repelling) forces between the first and second objects.

As shown in step 404, the actuator is used to move the second object to a first position via the extension bar. In the example shown in FIG. 4, the first position is closer to the first object as compared to the initial set-up in step 402. In this case, there are attracting forces between the first/second objects, and moving the second object closer to the first object causes the first object, and with it the diamagnetic rod, to move in the direction of (i.e., towards) the second object. By way of a non-limiting scenario, in this example the actuator is located to the right side of the PDL trap. Thus based on the attracting forces, moving the second object closer to the right side of the PDL trap will too attract the first object (and with it the diamagnetic rod) to the right side of the PDL trap. The amount by which the first object/diamagnetic rod is displaced within the trap is proportional to the (in this case attracting) force between the first/second objects and the position of the second object. The position of the second object is a factor since the forces between the first/second objects will be stronger the closer the first/second objects are to one another. Thus, to use a simple non-limiting example, in the initial set-up (see, for example, step 402), the first/second objects are likely far enough apart that there is no displacement of the first object/diamagnetic rod in the PDL trap, and the diamagnetic rod (due to the camelback magnetic potential) is resting at the middle of the PDL trap (i.e., $\Delta z=0$). In the first position, the distance between the first/second objects is reduced, and the effects of the attracting force between the first/second objects is sufficient to displace the first object/diamagnetic rod in the PDL trap. The second object can then be moved to one or more other positions either closer or farther away from the PDL trap to see what effect decreasing or increasing the distance between the first/second objects has on the displacement. One can then establish distance dependence laws for the object. To use a simple example to illustrate this concept, one could move the second object successively closer to the PDL trap until a maximum displacement of the first object/diamagnetic rod in the PDL trap occurs. The second object could then be moved successively farther away from the PDL until the first object/diamagnetic rod settles back at the center of the PDL trap. The displacement of the first object/diamagnetic rod in the PDL trap will scale relative to distances between this minimum and maximum distance, respectively.

As shown in step 404, the displacement (if any) of the first object/diamagnetic rod from the center of the PDL trap is measured. As will be described in detail below, a number of different techniques are contemplated herein for measuring the position of the first object/diamagnetic rod in the PDL trap, and hence any displacement. For example, optical sensing (such as via digital video capture or photodetectors) or capacitive sensing techniques may be employed.

As shown in step 406, the actuator is used to move the second object to a second position via the extension bar, and the displacement (if any) of the first object/diamagnetic rod in the PDL trap is again measured. The idea here is that, as provided above, the amount of displacement of the first object/diamagnetic rod in the PDL trap is analyzed as a function of the distance between the objects (which is controlled based on the position of the second object), and thus moving the second object to another position relative to the PDL trap (e.g., closer or farther away from the PDL trap as compared to the first position) can be used to deduce this distance dependence factor. For instance, using the example shown in FIG. 4 the second position is closer to the PDL trap than the first position. In this case, bringing the objects closer together in step 406 increases the displacement of the object/diamagnetic rod in the PDL trap. This is not always the case however. For instance, based on the attracting forces between the objects, the first position might result in the maximum amount of displacement achievable. In that case, bringing the objects closer together will not increase the displacement. Further, the increments in position shown in FIG. 4 are merely examples meant to illustrate the present techniques. It is to be understood that multiple other positions closer and/or farther away from the PDL trap can be evaluated in the same manner described, if so desired.

The distance dependence of the force can also be evaluated by moving the second object away from the PDL trap to a third position. See, for example, step 408. For instance, as in this example, once displacement of the first object/diamagnetic rod has been registered (e.g., at position 1 and/or position 2), the second object can then be moved back away from the PDL trap to analyze the distance dependency. Again, this can be done incrementally via one or more other positions not shown in the figure. Basically, as the objects are moved farther apart from one another, and thus the impact of the attracting force decreases relative to the magnetic camelback potential. As a result of the weakening attraction, the first object/diamagnetic rod will settle back towards the center of the PDL trap as shown in step 408. It is indicated in FIG. 4 that, as described above, the process can be iterated at a variety of different positions to evaluate the distance dependence of the force.

Figure 5:
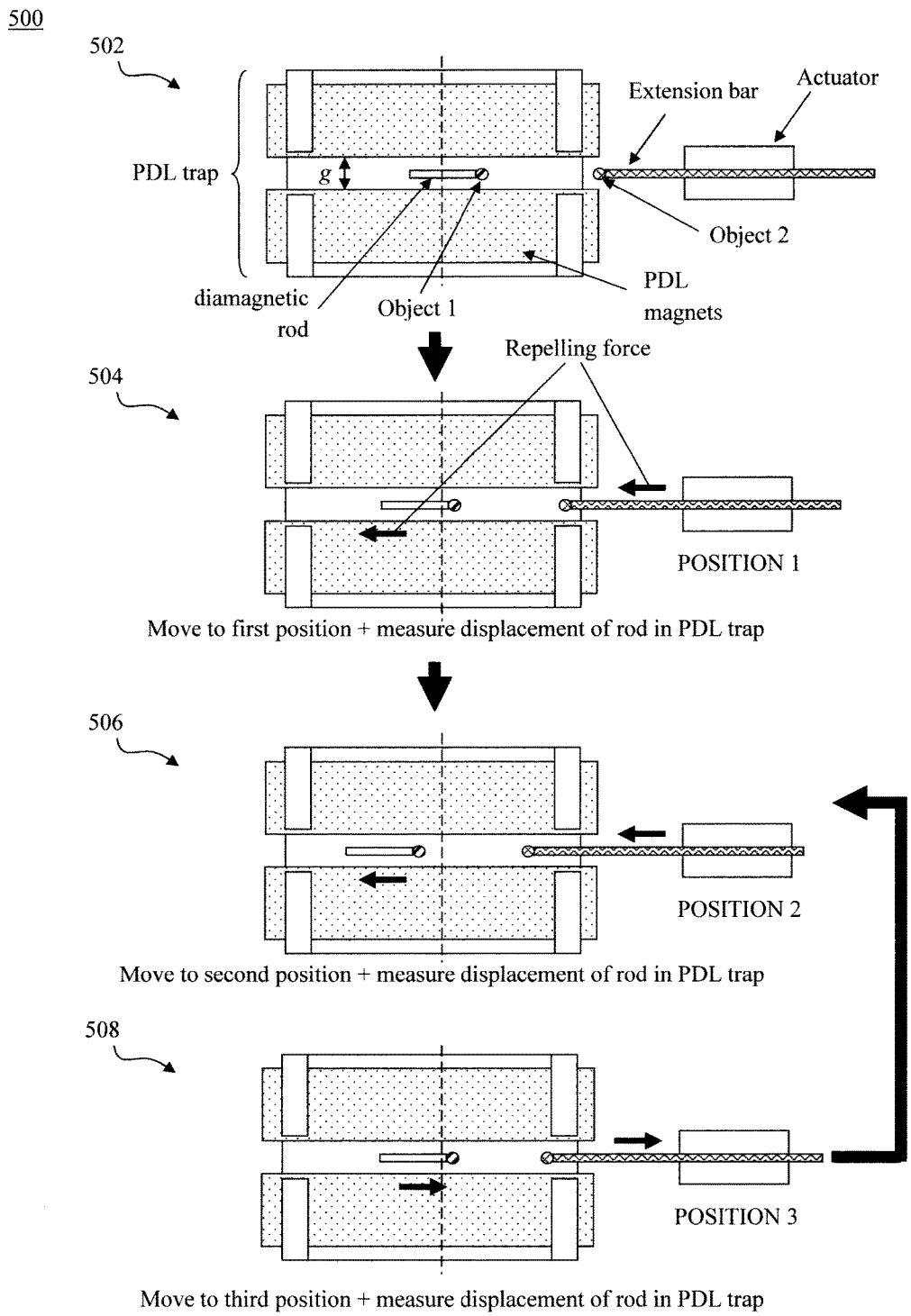
FIG. 5 is a top-down diagram illustrating an exemplary methodology for operating the present force gauge in the case where repelling forces between objects are present according to an embodiment of the present invention.

For completeness, FIG. 5 shows an exemplary methodology 500 (shown as top-view depictions of the force gauge) for operating the present force gauge in the case where repelling forces between the objects are present. In the same manner as described above, as shown in step 502, the present PDL force gauge is provided having a pair of cylindrical magnets mounted to a fixture (introducing a gap g between the magnets), a diamagnetic rod (e.g., a graphite rod) levitating above the magnets, and an actuator (e.g., a piezo ceramic actuator) with extension bar off to one side of the PDL trap. A first object of interest is attached to the diamagnetic rod, and a second object of interest is attached to the extension bar. See step 402 in FIG. 4.

As shown in step 504, the actuator is used to move the second object to a first position via the extension bar. In the example shown in FIG. 5, the first position is closer to the PDL trap as compared to the initial set-up in step 502. In this case, there are repelling forces between the first/second objects, and moving the second object closer to the first object causes the first object and the diamagnetic rod, to move away from the second object. In this example the actuator is located to the right side of the PDL trap. Thus based on the repelling forces, moving the second object closer to the right side of the PDL trap will repel the first object (and with it the diamagnetic rod) to the left side of the PDL trap. The amount by which the first object/diamagnetic rod is displaced within the trap is proportional to the (in this case attracting) force between the first/second objects and the position of the second object.

Thus, in the first position, the second object is brought closer to the PDL trap and the effects of the repelling force between the first/second objects is shown to be sufficient to displace the first object/diamagnetic rod in the PDL trap (it is assumed, as above, that with the initial set-up shown in step 502 the objects are far enough apart that the force between the objects does not result in any displacement of the first object/diamagnetic rod in the PDL trap). The second object can then be moved to one or more other positions either closer or farther away from the PDL trap to see what effect decreasing or increasing the distance between the first/second objects has on the displacement. One can then establish distance dependence laws for the object.

As shown in step 504, the displacement (if any) of the first object/diamagnetic rod in the PDL trap is measured (at the first position), and in step 506 the actuator is used to move the second object to a second position via the extension bar (in this example closer still to the PDL trap), and the displacement (if any) of the first object/diamagnetic rod in the PDL trap is again measured. The increments in position shown in FIG. 5 are merely examples meant to illustrate the present techniques and it is to be understood that multiple other positions closer and/or farther away from the PDL trap can be evaluated in the same manner described, if so desired. The idea here is that, as provided above, the amount of displacement of the first object/diamagnetic rod in the PDL trap is analyzed as a function of the distance between the objects (which is controlled based on the position of the second object), and thus moving the second object to another position relative to the PDL trap (e.g., closer or farther away from the PDL trap as compared to the first position) can be used to deduce this distance dependence factor. Depending on the strength of the force between the objects, there may be a point beyond which moving the second object closer to the PDL trap will result in further displacement of the first object/diamagnetic rod in the PDL trap.

The distance dependence of the force can also be evaluated by moving the second object back away from the PDL trap. See, for example, step 508 where the second object is moved to a third position. For instance, once displacement of first object/diamagnetic rod has been registered (e.g., at position 1 and/or position 2), the second object can then be moved back away from the PDL trap to analyze the distance dependency. Again, this can be done incrementally via one or more other positions not shown in the figure. As the objects are moved farther apart from one another, the impact of the attracting force decreases relative to the magnetic camelback potential and the first object/diamagnetic rod will settle back towards the center of the PDL trap as shown in step 508. As indicated in FIG. 5, the process can be iterated at a variety of different positions to evaluate the distance dependence of the force.

Figure 6:
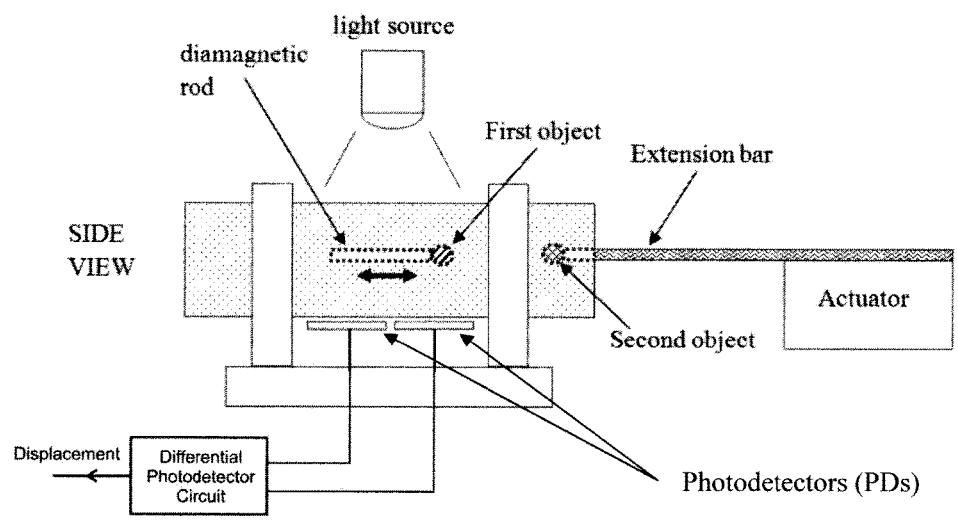
FIG. 6 is a side view diagram illustrating use of a light source and photodetectors to determine a position of a rod in the PDL trap according to an embodiment of the present invention.

Several different options for evaluating/measuring the position of the rod in the PDL trap are presented herein. In a first exemplary embodiment shown illustrated in FIG. 6, a plurality of photodetectors and a light source are used to detect the position of the rod in the PDL trap. Specifically, as shown in FIG. 6 a light source is placed above the PDL trap, and photodetectors (PDs) are placed below the PDL trap. These PDs are connected to a differential photodetector circuit that will subtract the photocurrent signals from both PDs, amplify them and yield the displacement signal of the trapped object. Suitable light sources include, but are not limited to, incandescent light bulb, light emitting diode and/or laser, and suitable photodetectors include, but are not limited to, semiconductor photodiodes and/or light-dependent-resistor (LDR).

The light source and the photodetectors are then used to determine the position of the rod in the PDL trap. Namely, as shown in FIG. 6, as the rod moves within the PDL trap it passes between the light source and the photodetectors. In this example, there are two photodetectors shown. However, this is for illustrative purposes only, and more (or fewer) photodetectors can be employed as needed. If the rod moves to the left side of the trap it will block light from the light source from reaching the photodetector on the left. However, light from the light source will reach the photodetector on the right. If the rod moves to the right side of the PDL trap it will block light from the light source from reaching the photodetector on the right. However, light from the light source will reach the photodetector on the left. See also, U.S. patent application Ser. No. 15/131,566 by Oki Gunawan, entitled "Parallel Dipole Line Trap with Variable Gap and Tunable Trap Potential," the contents of which are incorporated by reference as if fully set forth herein.

In another exemplary embodiment, the position of the rod in the PDL trap is detected using capacitive sensing techniques. See, for example FIG. 7. In general, capacitive sensing involves placing at least one pair of electrodes over the dipole line magnets of the PDL trap (such that the rod can move freely in and out from the pair of electrodes without touching the electrodes and still remain in a levitation state). According to an exemplary embodiment, each electrode pair includes a pair of electrode shells (see cross section view in FIG. 7) enclosing the (levitated) rod thus forming a capacitor whose value depends on the position of the rod. A capacitance meter is configured to measure the capacitance of the electrode shells. As the rod moves in the PDL trap, the capacitance changes. Hence, by measuring the capacitance one can determine the position of the rod in the PDL trap. See, for example, U.S. patent application Ser. No. 15/131,443 by Oki Gunawan, entitled "Voltage-Tunable 1D Electro-Magnet Potential and Probe System with Parallel Dipole Line Trap" (hereinafter "U.S. patent application Ser. No. 15/131,443"), the contents of which are incorporated by reference as if fully set forth herein.

Figure 7:
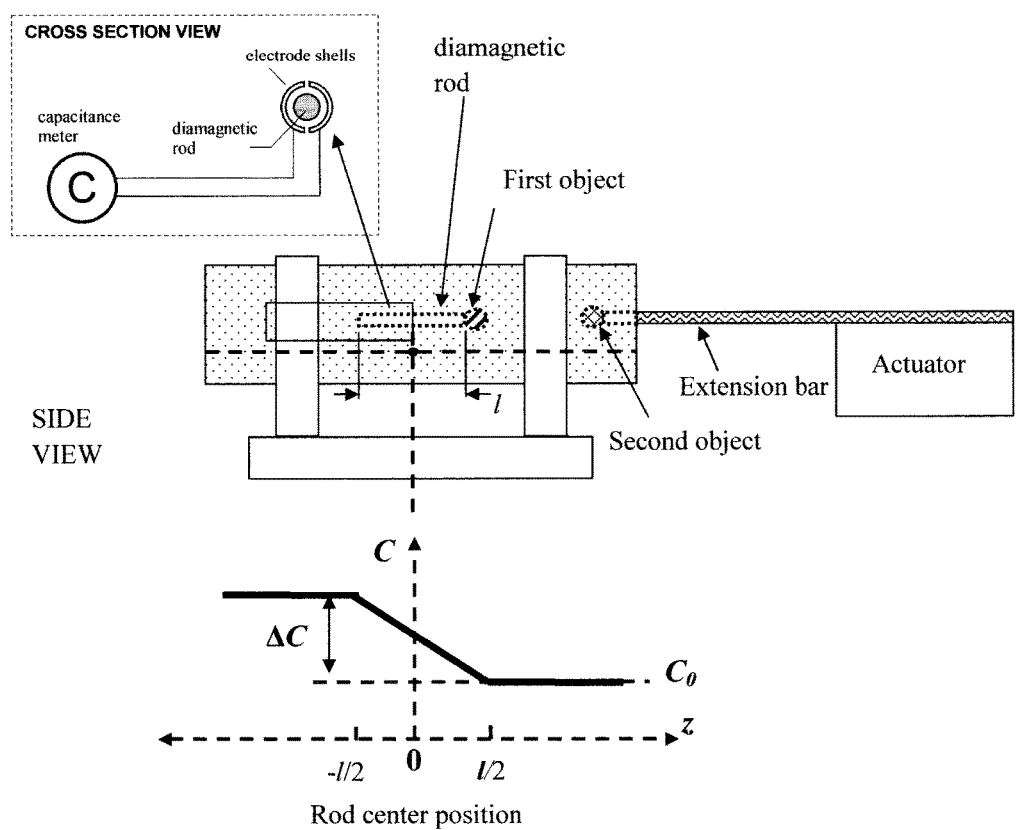
FIG. 7 is a side view diagram illustrating use of a single electrode capacitive sensing system to determine a position of a rod in the PDL trap according to an embodiment of the present invention.

As shown in FIG. 7, the pair of electrodes is employed over the PDL trap (off to one side of the PDL trap), and a capacitance meter is connected to the electrodes and is configured to measure the capacitance as explained above. As shown in FIG. 7, as the position of the rod in the PDL trap varies, its capacitance changes in the range of $-l/2 < z < l$, wherein $z$ is the centroid position of the rod and $l$ is the length of the rod.

As described in U.S. patent application Ser. No. 15/131, 443, the capacitance of a system like that shown in FIG. 7 can be given as follows:

$$C(z) = \begin{cases} C_0 + \Delta C & z < -l/2 \\ C_0 - \Delta C(z + l/2)/l & -l/2 < z < l/2 \\ C_0 & z > l/2 \end{cases} \quad (1)$$

wherein $C_0$ is the base capacitance when there is no rod, and $\Delta C$ is the maximum change in capacitance that occurs when the rod is completely within the electrodes. Thus, the position of the rod centroid z can be determined from the measured capacitance for $-l/2 < z < l/2$. Thus by knowing the rod displacement ($\Delta z$) and the movement of the actuator, the distance separation between the first and second object (r) can be determined.

Figure 8:
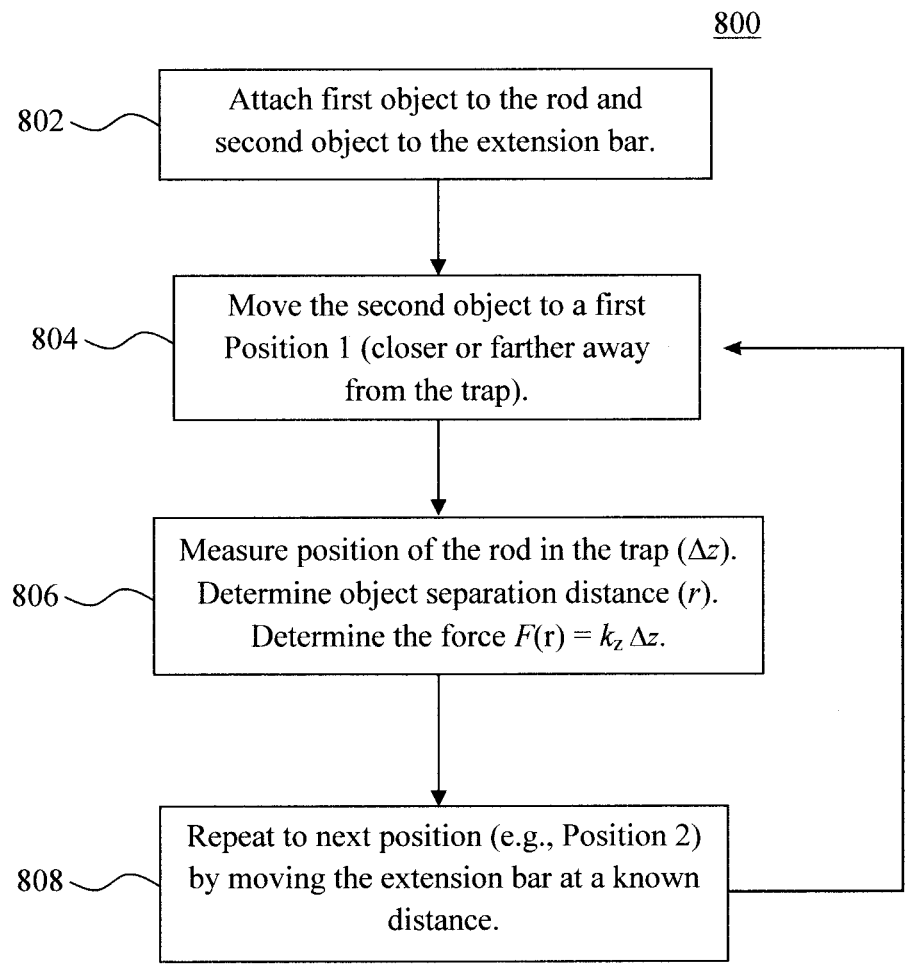
FIG. 8 is a diagram illustrating an exemplary methodology for force measurement using the present force gauge according to an embodiment of the present invention.

Given the above description, FIG. 8 provides an exemplary methodology 800 for measuring the force between two objects of interest (i.e., a first object and a second object) using the present force gauge. In step 802, the first object of interest is attached to the rod and the second object of interest is attached to the extension bar. As described above, the objects can include any two objects between which a force (e.g., attracting or repelling) is to be measured. By way of example only, the objects can include biomaterials such as proteins, genetic material (such as deoxyribonucleic acid (DNA) or ribonucleic acid (RNA) or inorganic material such as molecules and/or compounds, metals, etc.

In step 804, the extension bar is used to actuate the second object, moving the second object to a first position (Position 1) relative to the PDL trap. While the second object can be moved in step 804 either toward or away from the PDL trap, in this present example the first position is closer to the PDL trap. As described above, based on the force between the objects, this movement of the second object to the first position can cause the position of the first object and the rod in the PDL trap to change. For instance, an attracting force will cause the first object and rod to move in the PDL trap closer to the second object, while a repelling force will cause the first object and rod to move in the PDL trap away from the second object. In step 806, the position of the rod in the PDL trap is measured, i.e., with the second object at Position 1. As described above, the displacement of the rod is measured as a function of the object separation distance (r), i.e., the separation of the first and second objects. Thus, the force F as a function of distance r, i.e., F(r), between the first object and the second object can be determined.

In order to determine the distance dependence of the force measurement, see above, in step 808 the second object is next moved (via moving the extension bar a known distance) to at least one second position (Position 2) which is either closer to or farther away from the PDL trap than the first position (Position 1) and the position of the rod in the PDL trap is again measured, i.e., with the second object at Position 2. For instance, according to an exemplary embodiment, the second object is moved incrementally closer and/or farther away from to the PDL trap and after each movement the position of rod in the trap is measured.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A force gauge, comprising:
   parallel dipole line (PDL) trap having a pair of dipole line magnets and a diamagnetic rod levitating above the dipole line magnets;
   an actuator with an extension bar adjacent to the PDL trap;
   a first object of interest attached to the diamagnetic rod; and
   a second object of interest attached to the extension bar, wherein the actuator is configured to move the second object of interest toward or away from the PDL trap via the extension bar.

2. The force gauge of claim 1, wherein the pair of dipole line magnets are separated from one another by a gap g.

3. The force gauge of claim 1, wherein the first object of interest and the second object of interest are each selected from the group consisting of: proteins, genetic material, deoxyribonucleic acid, ribonucleic acid, molecules, compounds, metals and combinations thereof.

4. The force gauge of claim 1, wherein the actuator is configured to generate linear motion of the extension bar based on an applied voltage.

5. The force gauge of claim 1, wherein the actuator comprises a piezo ceramic actuator.

6. The force gauge of claim 1, further comprising:
   a light source above the PDL trap; and
   at least one photodetector beneath the PDL trap, opposite the light source, configured to detect a position of the diamagnetic rod in the PDL trap as the diamagnetic rod passes between the light source and the at least one photodetector.

7. The force gauge of claim 6, wherein the light source is selected from the group consisting of: an incandescent light bulb, a light emitting diode, a laser, and combinations thereof.

8. The force gauge of claim 6, wherein the at least one photodetector is selected from the group consisting of: a semiconductor photodiode, a light-dependent-resistor, and combinations thereof.

9. The force gauge of claim 1, further comprising:
   at least one pair of electrodes above the PDL trap such that the diamagnetic rod can pass between the at least one pair of electrodes and the pair of dipole line magnets.

10. The force gauge of claim 9, further comprising:
    a capacitance meter connected to the at least one pair of electrodes.

11. A method for force measurement, the method comprising:
    providing a force gauge comprising a PDL trap having a pair of dipole line magnets, a diamagnetic rod levitating above the dipole line magnets, and an actuator with an extension bar adjacent to the PDL trap;
    attaching a first object of interest to the diamagnetic rod;
    attaching a second object of interest to the extension bar;
    moving the second object of interest toward or away from the PDL trap via the extension bar; and
    measuring a displacement of the diamagnetic rod in the PDL trap as a function of a position of the second object of interest.

12. The method of claim 11, further comprising:
    moving the second object to a first position;
    measuring the displacement of the diamagnetic rod in the PDL trap when the second object is at the first position;
    moving the second object to a second position; and
    measuring the displacement of the diamagnetic rod in the PDL trap when the second object is at the second position.

13. The method of claim 12, wherein moving the second object to the first position comprises:
   moving the second object towards the PDL trap.

14. The method of claim 12, wherein the second position is closer to the PDL trap than the first position.

15. The method of claim 12, wherein the second position is farther away from the PDL trap than the first position.

16. The method of claim 11, wherein the force gauge further comprises a light source above the PDL trap, and at least one photodetector beneath the PDL trap, opposite the light source, and wherein measuring the displacement of the diamagnetic rod in the PDL trap further comprises:
   detecting a position of the diamagnetic rod in the PDL trap as the diamagnetic rod passes between the light source and the at least one photodetector.

17. The method of claim 11, wherein the force gauge further comprises at least one pair of electrodes above the PDL trap, and wherein measuring the displacement of the diamagnetic rod in the PDL trap further comprises:
   detecting a position of the diamagnetic rod in the PDL trap based on a change in capacitance between the at least one pair of electrodes as the diamagnetic rod passes between the at least one pair of electrodes.

18. The method of claim 11, wherein the pair of dipole line magnets are separated from one another by a gap g.

19. The method of claim 11, wherein the first object of interest and the second object of interest are each selected from the group consisting of: proteins, genetic material, deoxyribonucleic acid, ribonucleic acid, metals and combinations thereof.

20. The method of claim 11, further comprising:
   applying a voltage to the actuator to generate linear motion of the extension bar.

* * * * *